United States Patent [19]

Merz et al.

[11] 4,293,556

[45] Oct. 6, 1981

[54] ANALGESIC 2-(2-ALKOXY-ETHYL)-2'-HYDROXY-6,7-BENZOMORPHANS AND SALTS THEREOF

[75] Inventors: Herbert Merz, Ingelheim am Rhein; Klaus Stockhaus, Bingen, both of Fed. Rep. of Germany

[73] Assignee: Boehringer Ingelheim GmbH, Ingelheim, Fed. Rep. of Germany

[21] Appl. No.: 154,067

[22] Filed: May 28, 1980

Related U.S. Application Data

[63] Continuation of Ser. No. 52,433, Jun. 26, 1979, abandoned.

[30] Foreign Application Priority Data

Jun. 26, 1978 [DE] Fed. Rep. of Germany ....... 2828039

[51] Int. Cl.$^3$ .................. A61K 31/445; C07D 221/26
[52] U.S. Cl. ...................................... 424/267; 546/97
[58] Field of Search ........................... 546/97; 424/267

[56] References Cited

U.S. PATENT DOCUMENTS

| | | | |
|---|---|---|---|
| 3,417,094 | 12/1968 | Dexter | 546/97 |
| 3,499,906 | 3/1970 | Robinson et al. | 546/97 |
| 3,982,005 | 9/1976 | Merz et al. | 546/97 X |
| 4,020,164 | 4/1977 | Rahtz et al. | 546/97 X |

OTHER PUBLICATIONS

Chemical Abstracts, 87:201833u (1977) [Rahtz, D., et al., Eur. J. Med. Chem.-Chim. Ther. 1977, 12(3), 271-278].

Primary Examiner—Richard A. Schwartz
Attorney, Agent, or Firm—Hammond & Littell, Weissenberger & Muserlian

[57] ABSTRACT

Compounds of the formula

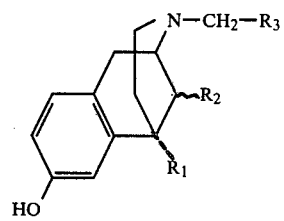

wherein
$R_1$ is methyl, ethyl or propyl;
$R_2$ is hydrogen, methyl or ethyl; and
$R_3$ is

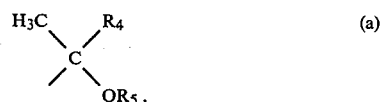 (a)

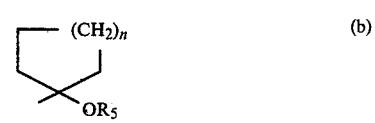

(b)

or

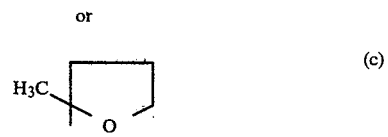 (c)

where
$R_4$ is hydrogen or methyl,
$R_5$ is methyl, ethyl or propyl, and
n is 1 or 2, and non-toxic, pharmacologically acceptable acid addition salts thereof. The compounds as well as the salts are useful as analgesics.

4 Claims, No Drawings

ANALGESIC 2-(2-ALKOXY-ETHYL)-2'-HYDROXY-6,7-BENZO-MORPHANS AND SALTS THEREOF

This is a continuation of copending application Ser. No. 52,433, filed June 26, 1979, now abandoned.

This invention relates to novel 2-(2-alkoxy-ethyl)-2'-hydroxy-6,7-benzomorphans and non-toxic acid addition salts thereof, to methods of preparing these compounds, to pharmaceutical compositions containing them as active ingredients, and to methods of using them as analgesics.

More particularly, the present invention relates to a novel class of 2-substituted 2'-hydroxy-6,7-benzomorphans represented by the formula

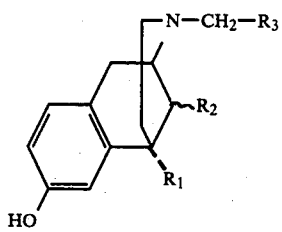
(I)

wherein
$R_1$ is methyl, ethyl or propyl;
$R_2$ is hydrogen, methyl or ethyl; and
$R_3$ is

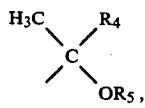  (a)

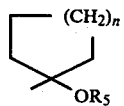  (b)

or

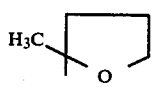  (c)

where
$R_4$ is hydrogen or methyl,
$R_5$ is methyl, ethyl or propyl, and
n is 1 or 2,
and non-toxic, pharmacologically acceptable acid addition salts thereof.

A preferred sub-genus thereunder is constituted by compounds of the formula

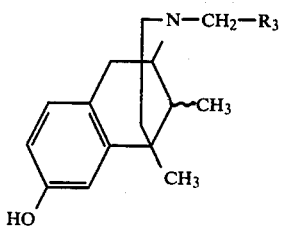
(Ia)

wherein $R_3$ has the meanings previously defined, and non-toxic, pharmacologically acceptable acid addition salts thereof.

In view of the above-indicated definition of the compounds of the formula I, the following situation results with respect to stereochemistry:

The norbenzomorphan precursors of the formula

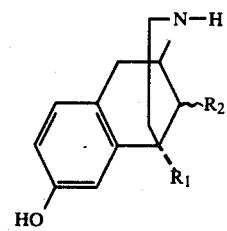
(II)

wherein
$R_1$ has the same meanings as in formula I, and
$R_2$ is hydrogen,
occur in racemic form and the two corresponding optical antipodes. When $R_2$ in formula II is alkyl, the substituents $R_1$ and $R_2$ may be in cis-configuration (5-alkyl-9α-alkyl-6,7-benzomorphans) or trans-configuration (5-alkyl-9β-alkyl-6,7-benzomorphans) with respect to the carbocyclic ring. In the α-series as well as in the β-series of compounds of the formula II each compound exists as a racemate and as the corresponding optical antipodes.

When the N-substituent $R_3$ in formula I is variant (a) and $R_4$ therein is hydrogen, or when $R_3$ is variant (c), chiral carbon atoms occur in the 2''-position. In those cases, the number of possible stereoisomers of the formula I doubles.

Preferred are the levo-rotatory compounds of the formula I. Especially preferred are the (−)-derivatives in which $R_3$ is in 2'' S-configuration.

The compounds of the formula I may be prepared by reducing a 2-acyl-2'-hydroxy-6,7-benzomorphan of the formula

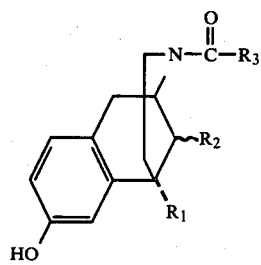
(III)

wherein $R_1$, $R_2$ and $R_3$ have the same meanings as in formula I, or a 2-acyl-2'-acyloxy-6,7-benzomorphan of the formula

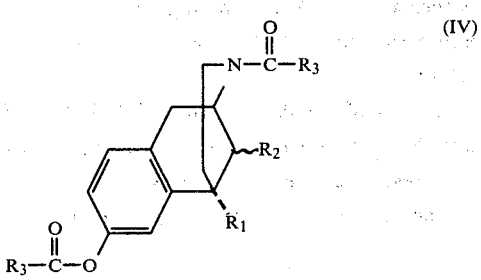

wherein $R_1$, $R_2$ and $R_3$ have the same meanings as in formula I.

For the reduction of an amide of the formula II or IV various known methods may be used. The use of complex hydrides as reducing agents has proved to be especially useful; with their aid the reaction can be carried out smoothly and simply. Although various complex hydrides may be considered for this reaction, the easily accessible lithium aluminum hydride is preferably used. In order to achieve complete reaction of the relatively expensive starting products of formulas III and IV, the complex hydride is used in the calculated quantity of preferably in excess, where in general an excess of 10 to 50% suffices. During reduction of an amide of the formula IV, not only the amide grouping but also the phenylester grouping is reduced, the latter being in general more easily attackable. It is of advantage to effect the reduction in a suitable inert solvent or mixture of solvents. For this purpose diethylether, diisopropylether and, in particular, tetrahydrofuran are preferred. The reaction temperature is variable within wide limits. It lies advantageously between 0° and 150° C., preferably between 20° and 75° C.

Working up of the reaction mixture and isolating and purifying the obtained novel compounds of the formula I is effected pursuant to known methods. If required, the obtained crude products may be purified by using special methods, for example column-chromatography, before they are crystallized in the form of the free base or suitable acid addition salts.

Depending upon the chosen reaction conditions and reaction partners, the obtained reaction products are either sterically uniform compounds or mixtures of racemic or optically active diastereoisomers.

Diastereoisomers may be separated, based on their differing chemical and physical properties, pursuant to known methods, for example by fractional crystallization. Racemic compounds may be separated into their corresponding optical antipodes by means of conventional methods for racemate splitting.

The acyl derivatives of the formula III and IV are obtained by reacting a norbenzomorphan of formula II with a carboxylic acid chloride of the formula

where $R_3$ has the above-mentioned meanings. Normally, the starting compounds of the formulas II and IV are produced in situ from compounds of the formulas II and V, and reacted without further purification.

The compounds embraced by formula I are organic bases and therefore form acid addition salts with inorganic or organic acids. Examples of non-toxic, pharmacologically acceptable acid addition salts are those formed with mineral acids such as hydrochloric acid, hydrobromic acid, hydriodic acid, hydrofluoric acid, sulfuric acid, phosphoric acid, nitric acid, or organic acids such as acetic acid, propionic acid, butyric acid, valeric acid, pivalic acid, caproic acid, oxalic acid, malonic acid, succinic acid, maleic acid, fumaric acid, lactic acid, pyruvic acid, tartaric acid, citric acid, malic acid, benzoic acid, p-hydroxy-benzoic acid, salicylic acid, p-aminobenzoic acid, phthalic acid, cinnamic acid, ascorbic acid, 8-chlorotheophylline, methanesulfonic acid, ethanephosphoric acid, or the like.

The following examples illustrate the present invention and will enable others skilled in the art to understand it more completely. It should be understood, however, that the invention is not limited solely to the particular examples given below.

EXAMPLE 1

(—)-(1R,5R,9R,2"R)-5,9-dimethyl-2'-hydroxy-2-(2-methoxypropyl)-6,7-benzomorphan hydrochloride (a) (1R,5R,9R,2"R)-5,9-dimethyl-2'-hydroxy-2-(2-methoxypropionyl)-6,7-benzomorphan 2.17 gm (0.01 mol) of (—)-5,9α-dimethyl-2'-hydroxy-6,7-benzomorphan were dissolved in 70 ml of methanol. The solution was admixed at room temperature, while stirring, with a solution of 2.5 gm of potassium carbonate in 4 ml of water and subsequently with 1.5 gm (0.0122 mol) of (+)-(R)-2-methoxy-propionyl chloride. Stirring was continued for 2 hours at room temperature, whereupon the reaction mixture was evaporated in vacuo. The evaporation residue was shaken with a mixture of 35 ml of chloroform and 15 ml of water, and the separated aqueous phase was extracted once more with 10 ml of chloroform. The combined chloroform phases were washed successively with 10 ml of 1 N HCl and 10 ml of water, dried with sodium sulfate and evaporated in vacuo. The residue consisted of the carboxylic acid amides required for the subsequent reduction.

(b) (—)-(1R,5R,9R,2"R)-5,9-dimethyl-2'-hydroxy-2-(2-methoxy-propyl)-6,7-benzomorphan hydrochloride The final evaporation residue of the preceding reaction step (a) was dissolved in 25 ml of absolute tetrahydrofuran and the solution was added dropwise, while stirring, over a period of 20 minutes to a suspension of 1.2 gm (0.032 mol) of lithium aluminum hydride in 15 ml of tetrahydrofuran cooled with ice-water. Then, the ice bath was removed, stirring was continued at room temperature for 1 hour, and the mixture was refluxed for 2 hours. Thereafter, it was cooled and, while stirring, the reaction mixture was admixed dropwise with 5 ml of water while cooling with ice-water. Then, 120 ml of saturated aqueous diammonium tartrate solution was added, the mixture was shaken in a separating funnel, and after settling the (upper) tetrahydrofuran phase was separated and the aqueous phase was extracted with 25 ml of chloroform. The evaporation residue of the tetrahydrofuran phase was combined with the chloroform extract, and the obtained chloroform solution was washed with water, dried with sodium sulfate and evaporated in vacuo. The evaporation residue was dissolved in 10 ml of methanol, the solution was admixed with 4.0 ml of 2.5 N ethanolic HCl and then with ether, until a lashing turbidity began. The title compound crystallized out of the solution. In order to complete crystallization, it was allowed to stand overnight at 0° C. Then, it was suction-filtered and the filter cake was washed first with methanol-ether 1:1 and then with ether, and dried at 80° C. Yield: 1.8 gm 55.2% of theory; m.p. 118° C. Recrystallization from 10 ml of methanol and 60 ml of ether yielded 1.4 gm of the substance with the unchanged melting point of 118° C. and a specific rotation of $[\alpha]_D^{22} = 83.8°$ (c=1, methanol).

EXAMPLE 2

(−)-(1R,5R,9R,2″S)-5,9-dimethyl-2′-hydroxy-2-(2-methoxypropyl-6,7-benzomorphan hydrochloride Analogous to Example 1, the title compound was obtained, starting from 2.17 gm (0.01 mol) of (−)-5,9α-dimethyl-2′-hydroxy-6,7-benzomorphan and 1.5 gm (0.0122 mol) of (−)-(S)-2-methoxy-propionyl chloride, with a yield of 2.6 gm (79.8% of theory) and a melting point of 141° C.

After recrystallization from methanol/ether, the melting point of the substance remained unchanged at 141° C., and the specific rotation was $[\alpha]_D^{22} = 57.0°$ (c=1, methanol).

EXAMPLE 3

(+)-(1S,5S,9S,2″R)-5,9-dimethyl-2′-hydroxy-2-(2-methoxypropyl)-6,7-benzomorphan hydrochloride Analogous to Example 1, the title compound was obtained, starting from 2.17 gm (0.01 mol) of (+)-5,9α-dimethyl-2′-hydroxy-6,7-benzomorphan and 1.5 gm (0.0122 mol) of (+)-(R)-2-methoxy propionyl chloride with a yield of 2.8 gm (85.9% of theory) and a melting point of 141° C. After recrystallization from methanol/ether, the substance still melted at 141° C. and had a specific rotation of $[\alpha]_D^{25} = +57.9°$ (c=1, methanol).

EXAMPLE 4

(−)-(1R,5R,9S,2″R)-5,9-dimethyl-2′-hydroxy-2-(2-methoxypropyl)-6,7-benzomorphan hydrochloride Analogous to Example 1, the title compound was obtained starting from 2.17 gm (0.01 mol) of (−)-5.9β-dimethyl-2′-hydroxy-6,7-benzomorphan and 1.5 gm (0.0122 mol) of (+)-(R)-2-methoxy-propionyl chloride, with a yield of 2.5 gm (76.7% of theory) and a melting point of 270° C.

After recrystallization from methanol/ether, the substance still melted at 270° C. and had a specific rotation $[\alpha]_D^{22} = -83.2°$ (c=1, methanol).

EXAMPLE 5

(−)-(1R,5R,9S,2″S)-5,9-dimethyl-2′-hydroxy-2-(2-methoxypropyl)-6,7-benzomorphan hydrochloride Analogous to Example 1, the title compound was obtained, starting from 2.17 gm (0.01 mol) of (−)-5,9β-dimethyl-2′-hydroxy-6,7-benzomorphan and 1.5 gm (0.0122 mol) of (−)-(S)-2-methoxy-propionyl chloride, with a yield of 2.4 gm (73.6% of theory) and a melting point of 254° C. After recrystallization from methanol/ether, the substance still melted at 254° C. and had a specific rotation $[\alpha]_D^{22} = 56.5°$ (c=1, methanol).

EXAMPLE 6

(−)-(1R,5R,9R,2″R)-5,9-diethyl-2′-hydroxy-2-(2-methoxypropyl)-6,7-benzomorphan oxalate (acid salt)

1.23 gm (0.005 mol) of (−)-5,9α-diethyl-2′-hydroxy-6,7-benzomorphan and 0.75 gm (0.0061 mol) of (+)-(R)-2-methoxypropionyl chloride, were reacted as described in Example 1 and yielded a reaction product which was reduced with LiAlH$_4$ as described there. The reduction product was isolated by chloroform extraction and evaporation of the washed and dried chloroform solution. The evaporation residue was dissolved in little methanol, the solution was acidified with 0.5 gm (0.055 mol) of oxalic acid and admixed with ether until turbidity began. The title compound crystallized out and, analogous to Example 1, yielded 1.4 gm (68.7% of theory) with a melting point of 206° C. Recrystallization from 20 ml of methanol and 50 ml of ether yielded 1.3 gm of substance with unchanged melting point.

EXAMPLE 7

(−)-(1R,5R,9R,2″S)-5,9-diethyl-2′-hydroxy-2-(2-methoxypropyl)-6,7-benzomorphan oxalate (acid salt)

Analogous to Example 6, the title compound was obtained, starting from 2.45 gm (0.01 mol) of (−)-5,9α-diethyl-2′-hydroxy-6,7-benzomorphan and 1.5 gm (0.0122 mol) of (−)-(S)-2-methoxy-propionyl chloride, with a yield of 3.2 gm (78.5% of theory) and a melting point of 146° C.; the latter did not change after recrystallization from 25 ml of ethanol and 50 ml of ether.

EXAMPLE 8

Diastereoisomeric mixture of (±)-(1R/S,5R/S,2″R/S)- and
(±)-(1R/S,5R/S,2″S/R)-2′-hydroxy-2-(2-methoxypropyl)-5-methyl-6,7-benzomorphan oxalate Analogous to Example 1 (a), 2.03 gm (0.01 mol) of (±)-2′-hydroxy-5-methyl-6,7-benzomorphane and 1.5 gm (0.0122 mol) of (±)-2-methoxypropionyl chloride are reacted and the reaction product is reduced with LiAlH$_4$, analogous to Example 1(b). As indicated there, the reaction product is isolated by chloroform extraction and evaporation of the washed and dried chloroform solution. For purification the evaporation residue is dissolved in 25 ml of chloroform and the solution is filtered via a chromatography column with 70 gm of aluminum oxide (activity III, neutral). The column is washed afterwards with chloroform, the united extracts are evaporated in vacuo. The evaporation residue consists of the diastereoisomeric mixture of bases, which is converted into the corresponding diastereoisomeric mixture of acid oxalates, analogous to example 6. Yield 2.3 gm = 62.9% of theory, melting point 188° (from methanol/ether).

EXAMPLE 9

Diastereoisomer mixture of (±)-1R/S,5R/S,2″R/S)- and
(±-(1R/S,5R/S,2″S/R)-5-ethyl-2′-hydroxy-2-(2-methoxypropyl)-6,7-benzomorphan oxalate Analogous to Example 8, the title compound was obtained starting from 2.17 gm (0.01 mol) of (±)-5-ethyl-2′-hydroxy-6,7-benzomorphan and 1.5 gm (0.0122 mol) of (±)-2-methoxypropionyl chloride, with a yield of 2.5 gm (65.9% of theory) and a melting point of 212° C. (from methanol/ether).

EXAMPLE 10

Diastereoisomer mixture of (±)-(1R/S, 5R/S, 2"R/S)- and (±)-(1R/S, 5R/S, 2"S/R)-2'-hydroxy-2-(2-methoxy-propyl)-5-n-propyl-6,7-benzomorphan Analogous to Example 8, starting from 2.31 gm (0.01 mol) of (±)-2'-hydroxy-5-n-propyl-6,7-benzomorphan and 1.5 gm (0.0122 mol) of (±)-2-methoxy-propionyl chloride, the diastereoisomer mixture of bases was obtained which was crystallized from 30 ml of methanol and 10 ml of water. Yield: 1.4 gm (46.1% of theory), melting point 158° C.

EXAMPLE 11

Diastereoisomer mixture of (±)-(1R/S, 5R/S, 9R/S, 2"R/S)- and (±)-(1R/S, 5R/S, 9R/S, 2"S/R)-9ethyl-2'-hydroxy-2-(2-methoxy-propyl)-5-methyl-6,7-benzomorphan Analogous to Example 8, starting from 2.31 gm (0.01 mol) (±)-9α-ethyl-2'-hydroxy-5-methyl-6,7-benzomorphan and 1.5 gm (0.0122 mol) (±)-2-methoxy-propionyl chloride the diastereoisomer mixture of bases was obtained, which was crystallized from 10 ml of methanol. Yield: 1.2 gm (39.5% of theory), melting pont 159°–160° C.

EXAMPLE 12

Diastereoisomer mixture of (±)-(1R/S, 5R/S, 9R/S, 2"R/S)- and (±)-(1R/S, 5R/S, 9R/S, 2"S/R)-5-ethyl-2'-hydroxy-2-(2-methoxy-propyl)-9-methyl-6,7-benzomorphan (a) (±)-5-ethyl-2,2'-di-(2-methoxy-propionyl)-9α-methyl-6,7-benzomorphan (diastereoisomer mixture)

A solution of 2.31 gm (0.01 mol) of 5-ethyl-2'-hydroxy-9α-methyl-6,7-benzomorphan in 40 ml of absolute methylene chloride and 4 ml of triethylamine was admixed, while stirring and ice-cooling, over a period of 20 minutes with 3.0 gm (0.0244 mol) of (±)-2-methoxy-propionyl chloride dissolved in 20 ml of absolute methylene chloride. Subsequently, the ice-bath was removed, stirring was continued at room temperature, and then the mixture was refluxed for 2 hours. Thereafter, it was cooled, and the methylene chloride solution is washed 3 times with 40 ml each of water. After drying with sodium sulfate, the organic phase was evaporated in vacuo. The evaporation residue consisted of a mixture of the diastereoisomers of the O-N-diacyl derivative of the used nor-compound.

(b) (±)-(1R/S, 5R/S, 9R/S, 2"R/S)- and (±)-(1R/S, 5R/S, 9R/S 2"S/R)-5-ethyl-2'-hydroxy-2-(2-methoxy-propyl)-9-methyl-6,7-benzomorphan (diastereoisomer mixture)

The evaporation residue obtained in the preceding reaction step was reduced with 1.8 gm (0.048 mol) of LiAlH4, analogous to Example 1 (b). As described there, the reaction product was isolated by extraction with chloroform. The combined chloroform extracts were washed with water, dried with sodium sulfate and evaporated in vacuo. The evaporation residue consisted of the diastereoisomer mixture mentioned in the title, which was recrystallized from 35 ml of methanol and 15 ml of water. Yield: 1.2 gm (39.5% of theory), m.p. 175°–176° C.

EXAMPLE 13

(±)-5,9α-dimethyl-2'-hydroxy-2-(2-methoxy-isobutyl)-6,7-benzomorphan 2.17 gm (0.01 mol) of (±)-5,9α-dimethyl-2'-hydroxy-6,7-benzomorphan and 1.7 gm (0.0125 mol) of 2-methoxyisobutyryl chloride were reacted analogous to to Example 1(a). As described there, the reaction product was isolated and reduced analogous to Example 1(b). As described there, the reduction product was extracted with chloroform. After washing, drying and evaporating the extracts, the evaporation residue was recrystallized from acetone. Yield: 1.4 gm (46.1% of theory), melting point 160° C.

EXAMPLE 14

(−)-5,9α-dimethyl-2'-hydroxy-2-(2-methoxyisobutyl)-6,7-benzomorphan

Analogous to Example 13, the title compound was obtained, starting from 2.17 gm (0.01 mol) of (−)-5,9α-dimethyl-2'-hydroxy-6,7-benzomorphan and 1.7 gm (0.0125 mol) of 2-methoxy-isobutyryl chloride, with a yield of 1.4 gm (46.1% of theory), melting point 86°–88° C. (from petroleum ether). After recrystallization from methanol/water, the substance melted at 91°–91.5° C. $[\alpha]_D^{25} = -114°$ (c=1, ethanol).

EXAMPLE 15

(±)-5,9β-dimethyl-2'hydroxy-2-(2-methoxy-isobutyl)-6,7-benzomorphan hydrochloride Analogous to Example 1, the title compound was obtained, starting from 3.26 gm (0.015 mol) of (+)-5,9β-dimethyl-2'-hydroxy-6.7-benzomorphan and 2.55 gm (0.0188 mol) of 2-methoxy-isobutyryl chloride, with a yield of 4.0 gm (78.5% of theory), melting point 226°–228° C.

EXAMPLE 16

(−)-5,9β-Dimethyl-2'-hydroxy-2-(2-methoxy-isobutyl)-6,7-benzomorphan hydrochloride Analogous to Example 1, the title compound was obtained, starting from 3.26 gm (0.015 mol) (−)-5,9β-dimethyl-2'-hydroxy-6,7-benzomorphan and 2.55 gm (0.0188 mol) of 2-methoxy-isobutyryl chloride, with a yield of 4.0 gm (78.5% of theory), melting point 226°–227° C.

EXAMPLE 17

(±)-2'-hydroxy-2-(2-methoxy-isobutyl)-5-methyl-6,7-benzomorphan

Analogous to Example 12, the title compound was obtained, starting from 2.03 gm (0.01 mol) of (±)-2'-hydroxy-5-methyl-6,7-benzomorphan and 3.0 gm (0.022 mol) of 2-methoxy-isobutyryl chloride, with a yield of 2.1 gm (72.6% of theory), melting point 99°–101° C. (petroleum ether).

EXAMPLE 18

(±)-5-ethyl-2'-hydroxy-2-(2-methoxy-isobutyl)-6,7-benzomorphan

Analogous to Example 13, the title compound was obtained, starting from 2.17 gm (0.01 mol) of (±)-2-ethyl-2'-hydroxy-6,7-benzomorphan and 1.7 gm (0.0125 mol) of 2-methoxyisobutyryl chloride, with a yield of 2.0 gm (65.9% of theory), melting point 104°–106° C. (petroleum ether).

EXAMPLE 19

(±)-2'-hydroxy-2-(2-methoxy-isobutyl)-5-propyl-6,7-benzomorphan

Analogous to Example 13, the title compound was obtained, starting from 2.31 gm (0.01 mol) of (±)-2'-hydroxy-5-propyl-6,7-benzomorphan and 1.7 gm (0.0125 mol) of 2-methoxy-isobutyryl chloride, with a yield of 2.4 gm 75.6% of theory), melting point 126°–128° C. (petroleum ether).

EXAMPLE 20

(±)-9α-ethyl-2'-hydroxy-2-(2-methoxy-isobutyl)-5-methyl-6,7-benzomorphan

Analogous to Example 13, the title compound was obtained, starting from 2.31 gm (0.01 mol) of (±)-9α-ethyl-2'-hydroxy-5-methyl-6,7-benzomorphan and 1.7 gm (0.0125 mol) of 2-methoxy-isobutyryl chloride, with a yield of 0.9 gm (28.4% of theory), melting point 80°–82° C. (petroleum ether).

EXAMPLE 21

(±)-5-ethyl-2'-hydroxy-2-(2-methoxy-isobutyl)-9α-methyl-6,7-benzomorphan hydrochloride Analogous to Example 1, the title compound was obtained, starting from 2.31 gm (0.01 mol) of (±)-5-ethyl-2'-hydroxy-9α-methyl-6,7-benzomorphan and 1.7 gm (0.0125 mol) of 2-methoxy-isobutyryl chloride with a yield of 1.3 gm (36.7% of theory), melting point 223° C. (ethanol/ether).

EXAMPLE 22

(±)-5,9α-diethyl-2'-hydroxy-2-(2-methoxyisobutyl)-6,7-benzomorphan oxalate

Starting from 2.45 gm (0.01 mol) of (±)-5,9α-diethyl-2'-hydroxy-6,7-benzomorphan and 3.0 gm (0.02 mol) of 2-methoxyisobutyryl chloride, by proceeding analogous to Example 13 the base corresponding to the title compound was obtained, which was converted into the oxalate analogous to Example 8. Yield 3.0 gm (71.2% of theory), melting point 128°–129° C. (ethanol/ether).

EXAMPLE 23

(±)-5,9α-dimethyl-2-(2-ethoxyisobutyl)-2'-hydroxy-6,7-benzomorphan

Analogous to Example 13, the title compound was obtained, starting from 2.17 gm (0.01 mol) of (±)-5,9α-dimethyl-2'-hydroxy-6,7-benzomorphan and 1.65 gm (0.011 mol) of 2-ethoxy-isobutyryl chloride, with a yield of 2.0 gm (63.0% of theory), melting point 135°–137° C. (methanol/water).

EXAMPLE 24

(±9-5,9α-dimethyl-2'-hydroxy-2-(2-n-propoxy-isobutyl)-6,7-benzomorphan hydrochloride Analogous to Example 1, the title compound was obtained, starting from 2.17 gm (0.01 mol) of (±)-5,9α-dimethyl-2'-hydroxy-6,7-benzomorphan and 1.8 gm (0.011 mol) of 2-n-propoxy-isobutyryl chloride, with a yield of 1.7 gm (46.2% of theory), melting point 185°–187° C.

EXAMPLE 25

(±)-5,9α-dimethyl-2'-hydroxy-2-(2-isopropoxy-isobutyl)-6,7-benzomorphan

Analogous to Example 13, the title compound was obtained, starting from 2.17 gm (0.01 mol) of (±)-5,9α-dimethyl-2'-hydroxy-6,7-benzomorphan and 1.8 gm (0.011 mol) of 2-isopropoxy-isobutyryl chloride, with a yield of 2.0 gm. (54.6% of theory), melting point 123°–125° C. (methanol/water).

EXAMPLE 26

(±)-5,9α-dimethyl-2'-hydroxy-2-(1-methoxy-1-cyclopentyl)methyl-6,7-benzomorphan

Analogous to Example 13, the title compound was obtained, starting from 2.17 gm (0.01 mol) of (±)-5,9α-dimethyl-2'-hydroxy-6,7-benzomorphan and 1.8 gm (0.011 mol) of 1-methoxy-cyclopentane-1-carboxylic acid chloride with a yield of 16 gm (48.6% of theory), melting point 88° C. (methanol/water).

EXAMPLE 27

(−)-5,9α-dimethyl-2'-hydroxy-2-(1-methoxy-1-cyclopentyl)methyl-6,7-benzomorphan

Analogous to Example 13, the title compound was obtained, starting from 2.17 gm (0.01 mol) of (−)-5,9α-dimethyl-2'-hydroxy-6,7-benzomorphan and 1.8 gm (0.011 mol) of 1-methoxy-cyclopentane-1-carboxylic acid chloride, with a yield of 1.8 gm (54.6% of theory), melting point 88°–90° C. (methanol/water).

EXAMPLE 28

(±)-5,9α-dimethyl-2'-hydroxy-2-(1-methoxy-1-cyclopentyl)methyl-6,7-benzomorphan hydrochloride Analogous to Example 1, the title compound was obtained, starting from 2.17 gm (0.01 mol) of (±)-5,9α-dimethyl-2'-hydroxy-6,7-benzomorphan and 1.8 gm (0.011 mol) of 1-methoxy-cyclopentane-1-carboxylic acid chloride, with a yield of 3.0 gm (82.0% of theory), melting point 232°–234° C.

EXAMPLE 29

(±)-5-ethyl-2'-hydroxy-2-(1-methoxy-1-cyclopentyl)-methyl-6,7-benzomorphan

Analogous to Example 13, the title compound was obtained, starting from 2.17 gm (0.01 mol) of (±)-5-ethyl-2'-hydroxy-6,7-benzomorphan and 1.8 gm (0.011 mol) of 1-methoxy-cyclopentane-1-carboxylic acid chloride, with a yield of 1.0 gm (30.4% of theory), melting point 122° C. (petroleum ether).

EXAMPLE 30

(±)-9α-ethyl-2'-hydroxy-2-(1-methoxy-1-cyclopentyl)-methyl-5-methyl-6,7-benzomorphan-oxalate Analogous to Example 22, the title compound was obtained, starting from 2.31 gm (0.01 mol) of (±)-9α-ethyl-2'-hydroxy-5-methyl-6,7-benzomorphan and 1.8 gm (0.01 mol) of 1-methoxy-cyclopentane-1-carboxylic acid choride, with a yield of 0.9 gm (20.7% of theory), melting pont 214° C. (ethanol/ether).

EXAMPLE 31

(±)-5-ethyl-2'-hydroxy-2-(1-methoxy-1-cyclopentyl)-methyl-9α-methyl-6,7-benzomorphan hydrochloride Analogous to Example 1, the title compound was obtained, starting from 2.31 gm (0.01 mol) of (±)-5-ethyl-2'-hydroxy-9α-methyl-6,7-benzomorphan and 1.8 gm (0.01 mol) of 1-methoxy-cyclopentane-1-carboxylic acid chloride, with a yield of 0.9 gm (23.7% of theory), melting point 222° C.

EXAMPLE 32

(±)-5,9α-dimethyl-2-(1-ethoxy-1-cyclopentyl)-methyl-2'-hydroxy-6,7-benzomorphan hydrochloride Analogous to Example 1, the title compound was obtained, starting from 2.17 gm (0.01 mol) of (±)-5,9α-dimethyl-2'-hydroxy-6,7-benzomorphan and 1.94 gm (0.011 mol) of 1-ethoxy-cyclopentane-1-carboxylic acid chloride, with a yield of 1.7 gm (44.7% of theory), melting point 200°-202° C.

EXAMPLE 33

(±)-5,9β-dimethyl-2-(1-ethoxy-1-cyclopentyl)-methyl-2'-hydroxy-6,7-benzomorphan hydrochloride Analogous to Example 1, starting from 2.17 gm (0.01 mol) of (±)-5,9β-dimethyl-2-hydroxy-6,7-benzomorphan and 1.94 gm (0.011 mol) of 1-ethoxy-cyclopentane-1-carboxylic acid chloride, the title compound was obtained with a yield of 2.2 gm (57.9% of theory), melting point 208°-210° C.

EXAMPLE 34

(±)-5,9α-dimethyl-2'-hydroxy-2-(1-methoxy-1-cyclohexyl)methyl-6,7-benzomorphan hydrochloride Analogous to Example 1, the title compound was obtained, starting from 2.17 gm (0.01 mol) of (±)-5,9α-dimethyl-2'-hydroxy-6,7-benzomorphan and 1.94 gm (0.011 mol) of 1-methoxy-cyclohexane-1-carboxylic acid chloride, with a yield of 1.3 gm (21.0% of theory), melting point 220° C.

EXAMPLE 35

(±)-5,9β-dimethyl-2'-hydroxy-2-(1-methoxy-1-cyclohexyl)methyl-6,7-benzomorphan hydrochloride Analogous to Example 1, the title compound was obtained, starting from 2.17 gm (0.01 mol) of (±)-5,9β-dimethyl-2'-hydroxy-6,7-benzomorphane and 1.94 gm (0.011 mol) of 1-methoxy-cyclohexane-1-carboxylic acid chloride, with a yield of 1.3 gm (34.2% of theory), melting point 267° C.

EXAMPLE 36

(−)-(1R, 5R, 9R, 2″R)-5,9-dimethyl-2'-hydroxy-2-(2-methyltetrahydrofurfuryl)-6,7-benzomorphan hydrochloride and (−)-(1R, 5R, 9R, 2″S)-5,9-dimethyl-2'-hydroxy-2-(2-methyltetrahydrofurfuryl)-6,7-benzomorphan (a) Mixture of the two diastereoisomeric (−)-5,9α-dimethyl-2'-hydroxy-2-(2-methyl-tetrahydro-2-furoyl)-6,7-benzomorphans (amide intermediate step)

A mixture of 10.87 gm (0.05 mol) of (−)-5,9α-dimethyl-2'-hydroxy-6,7-benzomorphan and 7.81 gm (0.06 mol) of racemic 2-methyl-tetrahydrofuran-2-carboxylic acid was dissolved in 50 ml of methanol while heating. The solution was evaporated in an atmosphere of flowing nitrogen on an oil bath at 60° C. Then, the temperature of the bath was increased while continuing to pass dry nitrogen over the solution and was maintained for 8 hours at 240° C. After cooling, the reaction product was dissolved in chloroform, and the solution was washed successively once with 2 N HCl and twice with water. Evaporation of the chloroform solution after drying with sodium sulfate, yielded an evaporation residue which consisted of a mixture of the diastereoisomeric amide intermediate products.

(b) (−)-(1R, 5R, 9R, 2″R)-5,9-dimethyl-2'-hydroxy-2-(2-methyl-tetrahydrofurfuryl)-6,7-benzomorphan hydrochloride The amide mixture obtained in the preceding reaction step was reduced with LiAlH$_4$ analogous to Example 1(b). The reduction product was dissolved in 25 ml of ethanol and 25 ml of 2 N ethanolic HCl. The solution was admixed with ether until turbidity began. The title compound separated out of the solution in crystalline form.

After 15 hours the crystals were suction-filtered off at 0° C., washed with ethanol/ether and dried at 80° C. Yield 1.8 gm (10.2% of theory based on the starting benzomorphan), melting point 245° C. (decomp.). After recrystallization from 20 ml of methanol and 80 ml of ether the substance melted at 276° C. (repeated recrystallization did not change the melting point any more). $[\alpha]_D^{25} = 77.1°$ (c=1.0, H$_2$O).

(c) (−)-(1R, 5R, 9R, 2″S)-5,9-dimethyl-2'-hydroxy-2-(2-methyltetrahydrofurfuryl)-6,7-benzomorphan The motor liquor of the first crystallization of the 2″R-diastereoisomer was evaporated in vacuo, and the residue was shaken with a mixture of 100 ml chloroform, 100 ml water and 5 ml of concentration ammonia. After having separated the chloroform phase, the latter was washed with water, dried with sodium sulfate and evaporated in vacuo. A solution of the evaporation residue in 20 ml toluene, diluted with petroleum ether (about 60 ml), precipitated crystals which were suction-filtered off after standing overnight in the refrigerator, washed with toluene/petroleum ether and dried at 80° C. The title compound was obtained with a yield of 3.0 gm (19.0% of theory, based on the starting benzomorphan); melting point 140°-141° C., which increased to 142° C. after recrystallization from toluene/petroleum ether.

$[\alpha]_D^{25} = -72.7°$ (hydrochloride, c=1.0, water, prepared from equivalent amounts of the base and HCl).

EXAMPLE 37

(1)-(1R, 5R, 9R, 2″R)-5,9-dimethyl-2'-hydroxy-2-(2-methyltetrahydrofurfuryl)-6,7-benzomorphan hydrochloride Analogous to Example 36, the title compound was obtained, starting from 1.09 gm (0.005 mol) of (−)-5,9α-dimethyl-2'-hydroxy-6,7-benzomorphan and 0.78 gm (0.006 mol) of R-2-methykl-tetrahydrofuran-2-carboxylic acid, with a yield of 0.37 gm (21.0% of theory), m.p. 276° C. (decomp.)

EXAMPLE 38

(−)-(1R, 5R, 9R, 2″S)-5,9-dimethyl-2′-hydroxy-2-(2-methyltetrahydrofurfuryl)-6,7-benzomorphan Starting from 1.09 gm (0.005 mol) of (−)-5,9α-dimethyl-2′-hydroxy-6,7-benzomorphan and 0.78 gm (0.006 mol) of S-2-methyl-tetrahydrofuran-2-carboxylic acid, the title compound was obtained by proceeding analogous to Example 36 and crystallizing the reaction product from toluene/petroleum ether. Yield: 0.3 gm (19.0% of theory); m.p. 142° C.

EXAMPLE 39

(±)-1R/S, 5R/S, 9R/S, 2″R/S)-5,9-dimethyl-2′-hydroxy-2-(2-methyl-tetrahydrofurfuryl)-6,7-benzomorphan hydrochloride and (±)-(1R/S, 5R/S, 9R/S, 2″R/S)-5,9-dimethyl-2′-hydroxy-2-(2-methyl-tetrahydrofurfuryl)-6,7-benzomorphan By reacting 10.87 gm (0.05 mol) of (±)-5,9α-dimethyl-2′-hydroxy-6,7-benzomorphan with 7.81 gm (0.06 mol) of racemic 2-methyl-tetrahydrofuran-2-carboxylic acid analogous to Example 36(a) a mixture of diastereoisomeric amide intermediate products was obtained, which was reduced analogous to Example 36(b). A mixture of the diastereoisomeric title compound was obtained, which was separated analogous to Example 36(b) and (c), giving the first of the two title compounds with a yield of 1.9 gm (10.8% of theory, based on the starting benzomorphan), melting point 257° C., and the second title compound with a yield of 2.0 gm (12.7% of theory, based on the starting benzomorphan), m.p. 120°–122° C., after recrystallization 128° C.

EXAMPLE 40

(−)-(1R,5R,9S,2″R)-5,9-dimethyl-2′-hydroxy-2-(2-methyltetrahydrofurfuryl)-6,7-benzomorphan hydrochloride and (−)-(1R,5R,9S,2″S)-5,9-dimethyl-2′hydroxy-2-(2-methyl-tetrahydrofurfuryl)-6,7-benzomorphan hydrochloride By reacting 10.85 gm (0.05 mol) of (−)-5,9β-dimethyl-2′-hydroxy-6,7-benzomorphan with 7.81 gm (0.06 mol) of racemic 2-methyl-tetrahydrofuran-2-carboxylic acid analogous to Example 36(a), a mixture of the diastereoisomeric amide intermediate products was obtained, which was reduced analogous to Example 36(b). The reduction product, isolated as described there, consisted of a mixture of the diastereoisomeric title compounds, which were separated as follows:

(a) Isolation of the (1R,5R,9S,2″R)-compound

The reduction product separated out of its hydrochloric acid solution as methanol-ether crystals (5.5 gm), which were recrystallized from 70 ml of methanol and 200 ml of ether. The 4.2 gm of substance thus obtained were recrystallized once more from 300 ml of ethanol, and yielded 3.2 gm of not completely pure title compound (18.2% of theory based on the starting benzomorphan). For complete purification, the hydrochloride (3.2 gm) was converted into the base, and the latter was recrystallized from 20 ml of toluene. 1.3 gm of base are obtained, which were dissolved with the calculated quantity of methanesulfonic acid in a little methanol. Out of the solution, admixed with ether, the methane sulfonate (2.0 gm, m.p. 212° C.) crystallized, which was recrystallized from 20 ml of methanol and 100 ml of ether (1.7 gm m.p. 212° C., thin-layer chromatographically pure). The methanesulfonate was converted into the hydrochloride via the base, which crystallized from methanol-ether. The completely pure first title compound was thus obtained: 1.5 gm, m.p. 279°–280° C. $[\alpha]_D^{25} = -73.9°$ C. (c=1.0, water).

(b) Isolation of the (1R,5R,9S,2″2)-compound

The mother liquor remaining from the separation of the first distereoisomer (5.5 gm) described under (a) was evaporated, and the evaporation residue was converted into the base, which was crystallized from 30 ml of toluene. The substance thus obtained (2.7 gm, m.p. 196°–197° C.) was recrystallized from toluene, whereby the pure base was obtained with a yield of 2.4 gm (15.2% of theory, based on the starting benzomorphan), m.p. 197°–198° C. The base yielded the second title compound out of a solution in methanol acidified with ethanolic hydrochloric acid, which was admixed with ether until turbidity began. Yielding 2.45 gm, m.p. 265° C. $[\alpha]_D^{25} = -83.9°$ (c=1.0, water).

EXAMPLE 41

(±)-(1R/S,5R/S,9S/R,2″S/R)-5,9-dimethyl-2′-hydroxy-2-(2-methyl-tetrahydrofurfuryl)-6,7-benzomorphan hydrochloride and (±)-(1R/S,5R/S,9S/R,2″R/S)-5,9-dimethyl-2′-hydroxy-2-(2-methyl-tetrahydrofurfuryl)-6,7-benzomorphan hydrochloride By reacting 10.85 gm (0.05 mol) of (−)-5,9β-dimethyl-2′-hydroxy-6,7-benzomorphan with 7.81 gm (0.06 mol) of racemic 2-methyltetrahydrofuran-2-carboxylic acid analogous to Example 37(a), a mixture of the diastereoisomeric amide intermediate products was obtained, which was reduced analogous to Example 36(b). The reduction product, isolated as described there, consisted of a mixture of the diastereoisomeric title compounds which was separated as follows:

(a) Isolation of the (1R/S,5R/S,9S/R,2″S/R-compound

The reduction product separated 2.5 gm of crystalline substance from a solution of 50 ml of toluene and 50 ml of petroleum ether, which melted at 167° C. and was obtained in completely pure form after recrystallization from 20 ml of toluene (1.8 gm m.p. 168° C.). Out of the mother liquor of the first crystallization another 0.7 gm of substance, melting point 168° C., was obtained. The total yield amounted to 2.5 gm (14.1% of theory, based on the starting benzomorphan). The base was dissolved in methanol with the calculated quantity of ethanolic hydrochloric acid. The first title compound was obtained from the solution admixed with ether until turbidity. Yield 2.4 gm, m.p. 276°–277° C.

(b) Isolation of the (IR/S,5R/S,9S/R,2″R/S)-compound

The mother liquors of the crystallization of the first diastereoisomer as base, described under (a), were evaporated, and the residue was crystallized from methanol-ether as methane sulfonate, which was obtained with a yield of 3.2 gm, m.p. 224° C. After recrystallization from 30 ml of methanol and 100 ml of ether (2.7 gm) it melted at 224° C. The methane sulfonate was converted into the hydrochloride via the base. The latter crystallized out of its solution in methanol-ether with a yield of 2.3 gm (12.9% of theory, based on the starting benzomorphan), melting point 269° C.

The compounds of the present invention, that is, those embraced by formula I and their non-toxic, pharmacologically acceptable acid addition salts, have useful pharmacodynamic properties. More particularly, they exhibit strong analgesic activities in warm-blooded animals, such as mice and rats, as determined by the writhing test and the hot-plate test.

The analgesic activity of the compounds of this invention exceeds that of morphine manifold. However, some aspects of the typical activity profile of morphine-like analgesics, such as the Straub's tail phenomenon and the locomotor effect, are missing. Those compounds of the formula I wherein $R_3$ is the 2-methyl-tetrahydrofurfuryl variant (c), exhibit morphine-antagonistic activity in addition to analgesic activity. This activity profile leads to the conclusion that the compounds of the present invention do not have a relevant physical dependence and abuse potential.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0083 to 1.67 mgm/kg body weight, preferably 0.016 to 0.33 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 42

Tablets

The tablet composition is compounded from the following ingredients:

| | |
|---|---|
| 5,9-Dimethyl-2'-hydroxy-2-2,methoxy-propyl)-6,7-benzomorphan hydrochloride | 20.0 parts |
| Lactose | 120.0 parts |
| Corn starch | 50.0 parts |
| Colloidal silicic acid | 2.0 parts |
| Soluble starch | 5.0 parts |
| Magnesium stearate | 3.0 parts |
| Total | 200.0 parts |

Preparation

The active ingredient is admixed with a portion of the excipients, and the mixture is granulated with the aid of an aqueous solution of the soluble starch. After drying, the granulate is admixed with the remainder of the excipients, and the mixture is compressed into 200 mgm-tablets. Each tablet is an oral dosage unit composition containing 20 mgm of the active ingredient.

EXAMPLE 43

Coated Pills

The pill core composition is compounded from the following ingredients:

| | |
|---|---|
| 5,9-Dimethyl-2'-hydroxy-2-(2-methoxy-propyl)-6,7-benzomorphan hydrochloride | 15.0 parts |
| Lactose | 100.0 parts |
| Corn starch | 95.0 parts |
| Colloidal silicic acid | 2.0 parts |
| Soluble starch | 5.0 parts |
| Magnesium stearate | 3.0 parts |
| Total | 220.0 parts |

Preparation

The ingredients are compounded as described in the preceding example, and the composition is compressed into 220 mgm-pill cores which are subsequently coated with a thin shell consisting essentially of a mixture of sugar, talcum and gum arabic. Each coated pill is an oral dosage unit composition containing 15 mgm of the active ingredient.

EXAMPLE 44

Suppositories

The suppository composition is compounded from the following ingredients:

| | |
|---|---|
| 5,9-Dimethyl-2'-hydroxy-2-(2-methoxy-propyl)-6,7-benzomorphan hydrochloride | 10.0 parts |
| Lactose | 150.0 parts |
| Suppository base (e.g. cocoa butter) | 1640.0 parts |
| Total | 1700.0 parts |

Preparation

The active ingredient and the lactose are admixed with each other, and the mixture is homogeneously dispersed in the molten suppository base. 1700 mgm-portions of the composition are poured into cooled suppository molds and allowed to harden therein. Each suppository is a rectal dosage unit composition containing 10 mgm of the active ingredient.

EXAMPLE 45

Hypodermic Solution

The solution is compounded from the following ingredients:

| | |
|---|---|
| 5,9-Dimethyl-2'-hydroxy-2-(2-methoxy-propyl)-6,7-benzomorphan hydrochloride | 1.0 parts |
| Sodium chloride | 10.0 parts |
| Double-distilled water q.s. ad | 1000.0 parts by vol. |

Preparation

The active ingredient and the sodium chloride are dissolved in the double-distilled water, and the solution is filtered until free from suspended particles, and the filtrate is filled under aseptic conditions into 1 cc-ampules which are subsequently sterilized and sealed.

The contents of each ampule are an injectable dosage unit composition containing 1 mgm of the active ingredient.

EXAMPLE 46

Drop Solution

The solution is compounded from the following ingredients:

| | |
|---|---|
| 5,9-Dimethyl-2'-hydroxy-2-(2-methoxy-propyl)-6,7-benzomorphan hydrochloride | 0.70 parts |
| Methyl p-hydroxy-benzoate | 0.07 parts |
| Propyl p-hydroxy-benzoate | 0.03 parts |
| Demineralized water | 100.0 parts by vol. |

Preparation

The active ingredient and the p-hydroxy-benzoates are dissolved in the demineralized water, the solution is filtered, and the filtrate is filled into 100 ml-bottles equipped with a dropping spout. 1 ml of the solution (20 drops) is an oral dosage unit composition containing 7 mgm of the active ingredient.

Any one of the other compounds embraced by formula 1 or a non-toxic, pharmacologically acceptable acid addition salt thereof may be substituted for the particular active ingredient in Examples 42 through 46. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A racemic or optically active compound of the formula

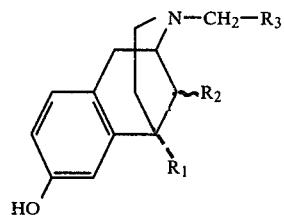

wherein
$R_1$ is methyl, ethyl or propyl;
$R_2$ is hydrogen, methyl or ethyl; and
$R_3$ is

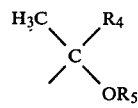 (a)

or

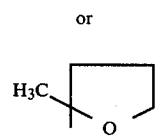 (b)

where
$R_4$ is hydrogen or methyl,
$R_5$ is methyl, ethyl or propyl, and
n is 1 or 2,
or a non-toxic, pharmacologically acceptable acid addition salt thereof.

2. A compound of claim 1, which is of the formula

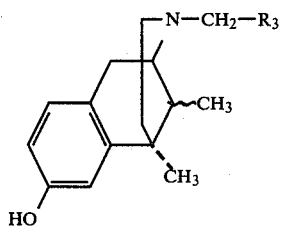

wherein $R_3$ has the meanings defined in claim 1 or a non-toxic, pharmacologically acceptable acid addition salt thereof.

3. An analgesic pharmaceutical dosage unit composition consisting essentially of an inert pharmaceutical carrier and an effective analgesic amount of a compound of claim 1.

4. The method of relieving pain in a warm-blooded animal in need thereof, which comprises perorally, parenterally or rectally administering to said animal an effective analgesic amount of a compound of claim 1.

* * * * *

UNITED STATES PATENT AND TRADEMARK OFFICE
CERTIFICATE OF CORRECTION

PATENT NO. : 4,293,556
DATED : October 6, 1981
INVENTOR(S) : HERBERT MERZ ET AL.

It is certified that error appears in the above—identified patent and that said Letters Patent is hereby corrected as shown below:

Column 4, line 24: "methox-" should read -- methoxy- --

Column 4, line 25: "ypropionyl" should read -- propionyl --.

Column 5, line 1: "lashing" should read -- lasting --.

Column 9, line 60 (Example 24): (±9-5,9α" should read -- (±)-5,9α --.

Column 10, lines 37 and 41 (Example 28): "(±)-5,9α" should read -- (±)-5,9β --.

Column 12, line 66: "methykl" should read -- methyl --.

Signed and Sealed this

Second Day of March 1982

[SEAL]

Attest:

GERALD J. MOSSINGHOFF

Attesting Officer  Commissioner of Patents and Trademarks